United States Patent [19]
Holick

[11] Patent Number: 5,395,829
[45] Date of Patent: Mar. 7, 1995

[54] COMPOSITIONS COMPRISING VITAMIN D LUMISTEROL ANALOG PRECURSORS

[75] Inventor: Michael F. Holick, Sudbury, Mass.

[73] Assignee: Trustees of Boston University, Boston, Mass.

[21] Appl. No.: 126,734

[22] Filed: Sep. 27, 1993

Related U.S. Application Data

[63] Continuation of Ser. No. 935,471, Aug. 27, 1992, abandoned, which is a continuation of Ser. No. 593,934, Oct. 4, 1990, abandoned.

[51] Int. Cl.⁶ ............................................. A61K 31/59
[52] U.S. Cl. ..................................... 514/167; 552/653
[58] Field of Search ................. 514/167, 171; 552/653

[56] References Cited

U.S. PATENT DOCUMENTS

| | | | |
|---|---|---|---|
| 3,702,810 | 11/1972 | Deluca et al. | 204/158 R |
| 4,230,701 | 10/1980 | Holick | 424/236 |
| 4,310,511 | 1/1982 | Holick | 424/59 |
| 4,397,847 | 8/1983 | Boris et al. | 424/236 |
| 4,410,515 | 10/1983 | Holick et al. | 424/180 |
| 4,490,226 | 12/1984 | Dauben | 204/159 |
| 4,521,410 | 6/1985 | Holick et al. | 514/26 |
| 4,619,829 | 10/1986 | Motschan | 424/128 |
| 4,634,692 | 1/1987 | Partridge et al. | 514/167 |
| 4,686,023 | 8/1987 | Stevens | 204/157.67 |
| 4,719,205 | 1/1988 | DeLuca et al. | 514/167 |
| 4,728,643 | 3/1988 | Holick | 514/167 |
| 4,749,710 | 6/1988 | Truitt et al. | 514/167 |
| 4,937,292 | 6/1990 | Slemon | 525/326.8 |

FOREIGN PATENT DOCUMENTS

| | | |
|---|---|---|
| 2301538 | 9/1976 | France . |
| 270070 | 7/1989 | Germany . |
| 285348 | 12/1990 | Germany . |

OTHER PUBLICATIONS

Abstract for Japanese Patent Publication No. JP-A-58 32 823, *Patent Abstracts of Japan* 7(114) (May 18, 1983).

Govseeva, N. N. et al., "Antirachitic Activity of Lumisterol", *Chemical Abstracts* 81 [Abstract 114422s] (1974).

Govseeva, N. N. et al., "Effect of Lumisterol₃ On Calcium Absorption in the Intestines and On Bone Tissue Calcification", *Chemical Abstracts* 81:442 [Abstract 168147z] (1974).

Holic, Michael, "The Cutaneous Photosynthesis of Previtamin D₃: A Unique Photoendocrine System", *J. Invest. Derm.* 77(1):51–58 (Jul. 1981).

Holick, Michael et al., "Isotachysterols and 25-Hydroxyisotachysterols: Analogs of 1,25-Dihydroxyvitamin D₃", *Science* 180:1001–1003 (May 25, 1973).

Holick, Michael, "On the Origin and Function of Provitamin D as a Unique Natural Ultra-Violet Sunscreen", *Clinical Research* 30(2):488A (Apr. 1982).

Tian, X. Q. et al., "1,25-Dihydroxyvitamin D₃: A Novel Agent for Wound Healing", *Clinical Research* 38(2):640A (Apr. 1990).

Webb et al., Influence of Season and Latitude on the Cutaneous Synthesis of Vitamin D₃: Exposure to Winter Sunlight in Boston and Edmonton Will Not . . . , *J. Clin. Endocrin. and Metab.* 67:373–378 (1988).

Reichenbaecher, M. et al., *Chem. Abstr.* 112:158731e (1990).

Kocienski, P. J. et al., *J. Chem. Soc. Perkin Trans I* 1400–4 (1980).

Dauben, W. G. et al., *J. Amer. Chem. Soc.* 104:355–356 (1982).

Dauben, W. G. et al., *J. Amer. Chem. Soc.* 104:5780–5781 (1982).

Holick, M. F. et al., *Science* 210:203–205 (Oct., 1980).

Holick M. F. et al., *Science* 211:590–593 (Feb., 1981).

MacLaughlin, J. A. et al., *Science* 216:1001–1003 (May, 1982).

Malatesta, V. et al., *J. Amer. Chem. Soc.* 103:6781–6783 (1981).

Shiina, E. et al., *Arch. Biochem. Biophys.* 220:90–94 (Jan., 1983).

Holock, M., *Biochem* 18:1003–1008 (1979).

*Primary Examiner*—Marianne M. Cintins
*Assistant Examiner*—T. J. Criares
*Attorney, Agent, or Firm*—Sterne, Kessler, Goldstein & Fox

[57] ABSTRACT

Compositions comprising lumisterol vitamin D analogs for enhancing the ability of an individual, exposed to sunlight, to produce vitamin D analogs via the skin are disclosed.

7 Claims, 4 Drawing Sheets

COMPOSITIONS COMPRISING VITAMIN D LUMISTEROL ANALOG PRECURSORS

This application is a continuation of application Ser. No. 07/935,471, filed Aug. 27, 1992, now abandoned, which is a continuation of application Ser. No. 07/593,934, filed Oct. 4, 1990, now abandoned.

FIELD OF THE INVENTION

The invention is in the field of cosmetics and medicinal chemistry. In particular, the present invention relates to topical compositions which provide vitamin D analogs throughout the year. In another aspect, the present invention relates to a method of producing previtamin D analogs. The topical compositions of the invention allow a user in the northern latitudes to produce previtamin D analogs on their skin even when exposed to low energy sunlight in the winter as well as in the morning and evening throughout the year. The method employs tachysterol and lumisterol analogs which photoisomerize to previtamin D analogs when exposed to low levels of ultraviolet radiation.

BACKGROUND OF THE INVENTION

Vitamin $D_3$ is a derivative of provitamin $D_3$ (7-dehydrocholesterol), the immediate biological precursor of cholesterol. With adequate exposure to sunlight, dietary supplements are not normally required. Holick et al. in Braunwald et al., Harrison's Principles of Internal Medicine, 11th ed. McGraw-Hill (1987), pp. 1857–69. However, not all individuals are exposed to the adequate levels of sunlight, especially in the winter.

When skin is exposed to sunlight or artificial sources of ultraviolet (UV) radiation, the UV radiation penetrates the epidermis and causes a variety of biochemical reactions. Included in these reactions are the transformation of provitamin $D_3$ to vitamin $D_3$. The electromagnetic energy having wavelengths between 290 and 315 nm is absorbed by provitamin $D_3$ resulting in its fragmentation to previtamin $D_3$. Although previtamin $D_3$ is biologically inert, it is thermally labile and spontaneously undergoes a temperature-dependent rearrangement to form the thermally stable vitamin $D_3$. After biosynthesis, vitamin $D_3$ is translocated from the epidermis into the circulation via a vitamin-D binding protein. Holick et al., Science 211:590–593 (1981); Holick et al. in Braunwald et al., Harrison's Principles of Internal Medicine, 11th ed., McGraw-Hill (1987), pp. 1857–69.

Factors that are frequently considered as affecting the cutaneous synthesis of vitamin $D_3$ include age, altitude, geographical location, time of day and area of exposure to sunlight. Common to most of these factors is the availability of the requisite amount of ultraviolet radiation with energies between 290 and 315 nm which is necessary to convert provitamin $D_3$ to vitamin $D_3$. MacLaughlin et al., Science 216:1001–1003 (1982).

The availability of vitamin D precursor in the skin and its photo-induced transformation to previtamin $D_3$ and then to vitamin $D_3$ is an efficient physiological source of and mechanism for the replenishment of vitamin $D_3$. However, during the winter in northern latitudes, sunlight does not contain enough high energy ultraviolet radiation to convert provitamin $D_3$ (7-dehydrocholesterol) in human skin to previtamin $D_3$ (Webb, Kline and Holick, J. Clin. Endocrinol. Met. 67:373–378 (1988)). As a result, individuals in these latitudes cannot make vitamin $D_3$ in their skin, even when they are exposed to sunlight. The lack of adequate exposure to ultraviolet radiation gives rise to the possibility of serious vitamin D deficiency, a breakdown in blood calcium regulation with concomitant hypocalcemia and bone calcium wasting.

The availability of the vitamin D precursor in the skin and its photo-induced transformation to previtamin $D_3$, and then to vitamin $D_3$, is an efficient physiological source of, and mechanism for the replenishment of vitamin $D_3$. Previously, it was thought that the only method of producing previtamin $D_3$ was to transform provitamin $D_3$. This transformation requires sunlight or artificial UV light in the region of 290–315 nm. Therefore, in areas where the available light energy is below this range (wavelengths greater than 316 nm), the transformation does not occur to any significant extent. Kobayashi et al., J. Nutr. Sci. Vitaminol. 19:123 (1973).

It has been disclosed (Holick, M., Transactions of the Association of American Physicians, 42:54–63 (1979); Molecular Endocrinology; MacIntyre and Szelke, eds.; Elsevier/North Holland Biomedical Press (1979), pp.301–308) that the topical application of hydroxylated metabolites of provitamin D compounds to the skin combined with U.V. phototherapy is a method for the sustained administration of vitamin D metabolites to patients who suffer vitamin D metabolic disorders. When the hydroxylated provitamins are applied and irradiated with ultraviolet radiation, they convert to hydroxylated previtamins which then thermally isomerize to the hydroxylated vitamin D. This work is also disclosed in Holick et al., New England Journal of Medicine 301:349–354 (1980) and U.S. Pat. No. 4,310,511 (Jan. 12, 1982).

1,25-Dihydroxyvitamin $D_3$ and its analogs have been shown to be powerful antiproliferative agents which are effective for the treatment of the hyperproliferative disorder psoriasis (DeLuca, H. Fed. Proc. Am. Soc. Biol. 2:224–236 (1988); Holick in DeGroot et al., Endocrinology 2:902–926, Grune and Stratton, New York, N.Y., (1988); Morimoto et al., Br. J. Dermatol. 115:421–429 (1986); Holick, Arch. Dermatol. 125:1692–1697 (1989)).

Hungarian Patent No. 102,939 discloses cosmetic creams containing provitamin D (such as ergosterol) which, when irradiated with ultraviolet rays, are transformed into vitamin D.

MacLaughlin et al., Science 216:1001–1003 (1982), disclose the synthesis of previtamin $D_3$ from provitamin $D_3$ in human skin and in an organic solvent after exposure to narrow-band radiation or simulated solar radiation. When human skin or an organic solvent containing provitamin $D_3$ were exposed to 295 nm radiation, up to 65% of the provitamin $D_3$ was converted to previtamin $D_3$. The authors further disclose that the optimum wavelength for the production of previtamin $D_3$ is between 295 nm and 300 nm.

Dauben et al., J. Am. Chem. Soc. 104:5780–5781 (1982); J. Am. Chem. Soc. 104:355–356 (1982), disclose the effect of wavelength on the photochemistry of provitamin $D_3$ and the effect of wavelength on the production of previtamin $D_3$. The authors found that when provitamin $D_3$ is exposed to light in the range of 254 nm, it is converted to a variety of photoproducts, the major portion being about 75% tachysterol. This mixture was then exposed to either 300 nm of light, broad-band 350 nm light or 355 nm light to give a build up of previtamin $D_3$. Dauben et al. conclude that if provitamin $D_3$ is first irradiated at 0° C. with 254 nm light to give a quasi photostationary state of provitamin $D_3$, previtamin $D_3$, tachysterol and lumisterol, and the mixture is thereafter irradiated (0° C.) with 350 nm light, a maximum of 83% previtamin $D_3$ is produced.

Malatesta et al., *J. Amer. Chem. Soc.* 103:6781–6783 (1981), disclose the effects of different UV wavelengths on the relative quantities of photoproducts produced from provitamin $D_3$.

Holick et al. disclose that the photochemical conversion of previtamin $D_3$ to lumisterol and tachysterol is the major factor that prevents vitamin $D_3$ intoxication after a single prolonged exposure to the sun. Holick et al., *Science* 211:590–592 (1981). The corollary to this finding is that lumisterol and tachysterol are two biologically inert products thought to be sloughed off the skin during the natural turnover of the epidermal cells.

Provitamin $D_2$ (ergosterol) is the precursor of vitamin $D_2$. Vitamin $D_2$ is one of the major forms of vitamin D that is used to fortify foods such as milk and multivitamins.

SUMMARY OF THE INVENTION

The present invention is related to the discovery that topical formulations comprising lumisterol and tachysterol analogs are effective means of providing previtamin D analogs to individuals. The present invention utilizes the low energy UV photoconversion of lumisterol and tachysterol analogs to previtamin D analogs as a method of producing vitamin D analogs in the skin. It is this novel finding that solves the problem of producing vitamin D analogs via the skin in areas of low energy sunlight.

In particular, the invention is directed to lumisterol and tachysterol analogs which are convertible to vitamin D analogs in the presence of low energy UV light. The invention is also directed to pharmaceutical compositions containing an effective amount of lumisterol and or tachysterol analogs and a pharmaceutically effective carrier.

The invention is also directed to a method for providing vitamin D analogs to an individual by administering to the individual a pharmaceutical composition of the invention.

The invention is also directed to a method of treating hyperproliferative disorders of the skin including psoriasis, healing wounds and inhibiting scar formation with the pharmaceutical compositions of the invention.

The invention is also directed to the treatment of ulcers such as diabetic ulcers of the feet, decubitus ulcers (bed sores), genito-urinary ulcers, and ulcerative keratitis with the pharmaceutical compositions of the invention.

DESCRIPTION OF THE PREFERRED EMBODIMENTS

Figure 1:
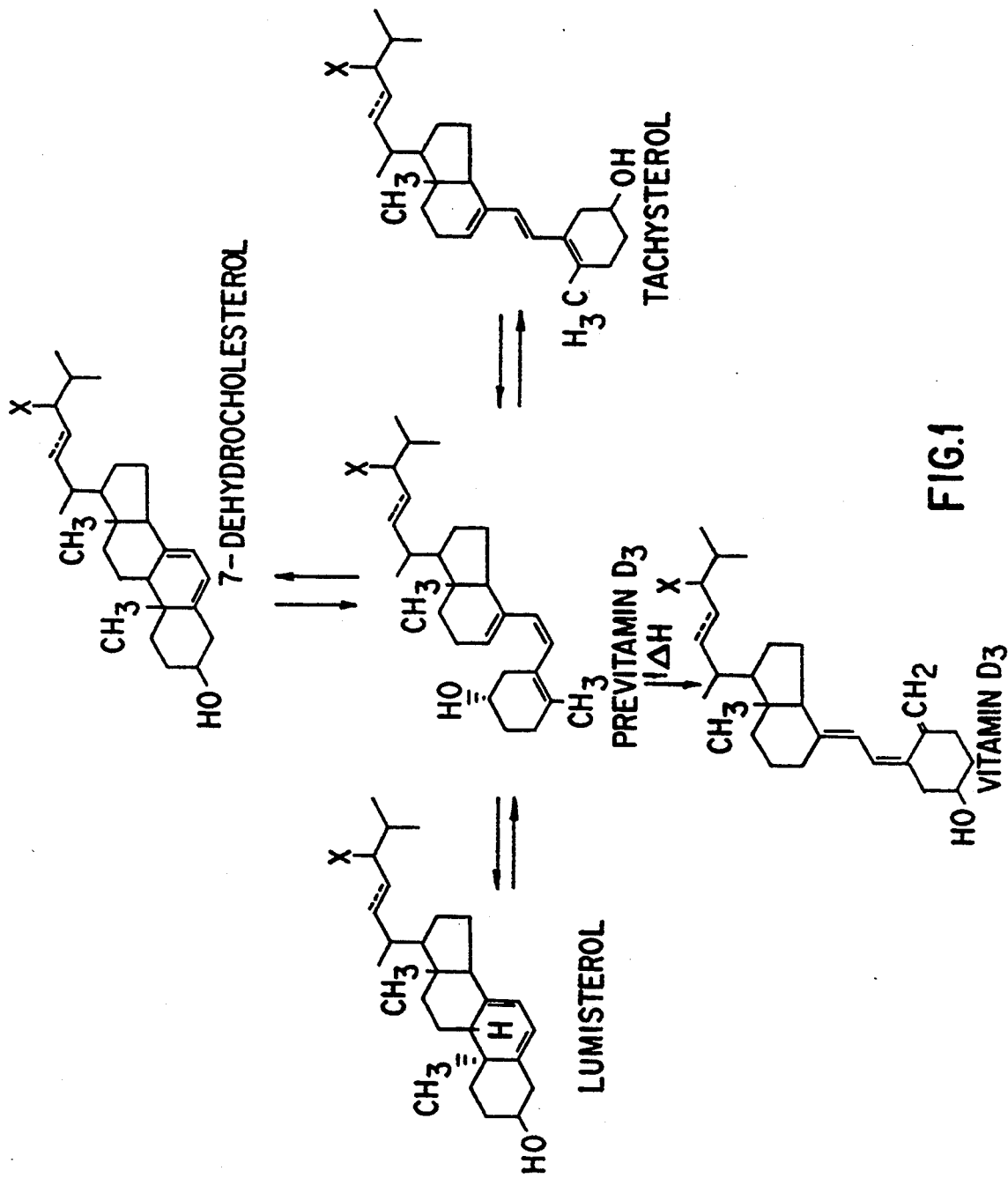
FIG. 1 illustrates the photochemical conversion of provitamin D to vitamin D and the concomitant production of lumisterol and tachysterol. When the bond between C-22 and C-23 is a single covalent bond and X is hydrogen, the compounds belong to the $D_3$ family, e.g. vitamin $D_3$. Where the bond between C-22 and C-23 is a double covalent bond and X is methyl, the compounds belong to the $D_2$ family, e.g. vitamin $D_2$.

The present invention provides for a method of healing wounds and inhibiting scar formation and treating hyperproliferative disorders of the skin including psoriasis. Wounds to the external epithelium include cuts, punctures and lacerations, including corneal lacerations. The invention also provides for the treatment of ulcers such as diabetic ulcers of the feet, decubitus ulcers (bed sores), genito-urinary ulcers, and ulcerative keratitis. Ulcerative keratitis is caused, for example, by extended wear of contact lenses.

Genito-urinary ulcers treatable with the tachysterol and lumisterol analogs of the invention include those caused by, for example, herpes simplex virus as well as other viral, fungal and bacterial infections. See Harrison's *Principles of Internal Medicine*, E. Braunwald et al. (eds.); McGraw-Hill Book Co., New York, N.Y., 1987, pp. 514–516.

The active compounds utilized in the present invention are tachysterol and lumisterol analogs, either alone or in combination. The lumisterol and tachysterol derivatives have the following Formulae (I) and (II), respectively:

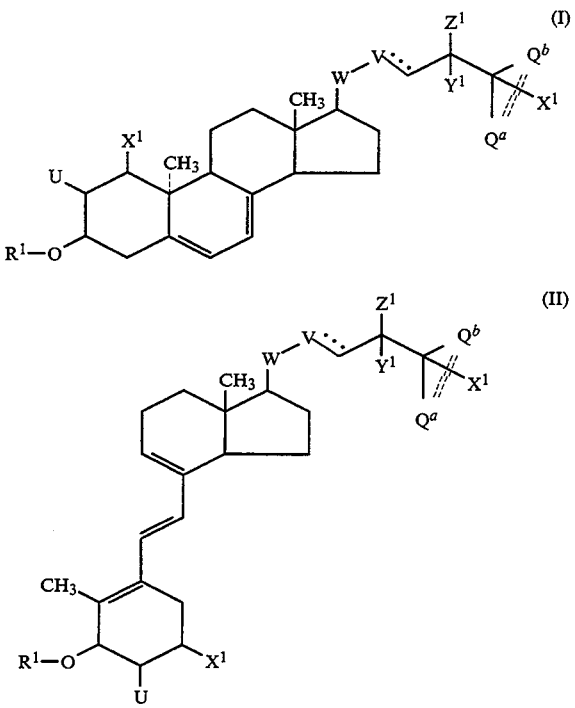

wherein the bond between carbons C-22 and C-23 is single or double bond;
$Y^1$ is hydrogen, F, $CH_3$, $CH_2CH_3$ or $X^1$;
U is hydrogen, —OH or —O—($C_2$–$C_4$ alkyl)—OH;
$Z^1$ is F, H or $X^1$;
$Q^a$ is $CF_3$ or $CH_2X^1$;
$Q^b$ is $CF_3$ or $CH_3$;
wherein $X^1$ is selected from the group consisting of hydrogen, —OH and $OR^1$;
wherein $R^1$ is hydrogen or a straight or branched chain glycosidic residue containing 1–20 glycosidic units per residue, or $R^1$ is an orthoester glycoside moiety of the Formula (III):

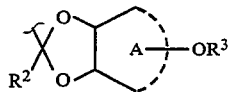

(III)

wherein A represents a glucofuranosyl or glucopyranosyl ring;

$R^2$ is hydrogen, lower $C_1$-$C_4$ alkyl or aryl, with the proviso that aryl is phenyl or phenyl substituted by chloro, fluoro, bromo, iodo, lower $C_1$-$C_4$ alkyl, $C_1$-$C_4$ alkoxy; or naphthyl; and $R^3$ is hydrogen or a straight or branched chain glycosidic residue containing 1–20 glycosidic units per residue;

W is CH—$CH_3$ or O;

V is $CH_2$ or O;

with the proviso that both W and V are not both O; and "= = =" is either a single bond between $Q^a$ and $Q^b$ or hydrogen atom on $Q^a$ and $Q^b$.

These compounds are photoisomers of previtamin D analogs, the precursor of biologically active vitamin D analogs. Examples of particular vitamin D analogs are taught, for example, by Holick et al., U.S. Pat. No. 4,310,511 (Jan. 12, 1982); Partridge et al., U.S. Pat. No. 4,634,692 (1987); Yamada, J. P. Publication No. J5 5111-460; DeLuca et al., U.S. Pat. No. 4,719,205 (1988); Holick et al., U.S. Pat. No. 4,410,515 (1983); Holick et al., U.S. Pat. No. 4,521,410 (1985); Holick et al., U.S. Pat. No. 4,230,701; and Shiina et al., *Arch. Biochem. Biophys.* 220:90 (1983), the disclosures of which are fully incorporated by reference herein. Methods for making the corresponding glycosidic and orthoester glycoside vitamin D analogs are taught, for example, by Holick et al., U.S. Pat. Nos. 4,410,515 and 4,521,410, the disclosures of which are fully incorporated by reference herein. The corresponding tachysterol and lumisterol analogs may be prepared by photoisomerization of the requisite provitamin D analog as disclosed by Holick et al., *Biochem.* 18:1003–1008 (1979), which is fully incorporated by reference herein.

Examples of tachysterol and lumisterol analogs include 1-hydroxytachysterol$_2$, 1-hydroxytachysterol$_3$, 1-hydroxylumisterol$_2$, 1-hydroxylumisterol$_3$, 1,24-dihydroxytachysterol$_2$, 1,24-dihydroxytachysterol$_3$, 1,24-dihydroxylumisterol$_2$, 1,24-dihydroxylumisterol$_3$, 1,25-dihydroxytachysterol$_2$, 1,25-dihydroxytachysterol$_3$, 1,25-dihydroxylumisterol$_2$, 1,25-dihydroxylumisterol$_3$, 24,25-dihydroxytachysterol$_2$, 24,25-dihydroxytachysterol$_3$, 24,25-dihydroxylumisterol$_2$, 24,25-dihydroxylumisterol$_3$, 25,26-dihydroxytachysterol$_2$, 25,26-dihydroxytachysterol$_3$, 25,26-dihydroxylumisterol$_2$, 25,26-dihydroxylumisterol$_3$, 1,24,25-trihydroxytachysterol$_2$, 1,24,25-trihydroxytachysterol$_3$, 1,24,25-trihydroxylumisterol$_2$, 1,24,25-trihydroxylumisterol$_3$, 2-β-(3-hydroxypropoxy)-1 alpha,25-dihydroxytachysterol$_2$, 2-β-(3-hydroxypropoxy)-1 alpha,25-dihydroxytachysterol$_3$, 2-β-(3-hydroxypropoxy)-1 alpha,25-dihydroxylumisterol$_2$, 2-β-(3-hydroxypropoxy)-1 alpha,25-dihydroxylumisterol$_3$, as well as the side chain fluoro derivatives of 1,25-dihydroxytachysterol$_2$, 1,25-dihydroxytachysterol$_3$, 1,25-dihydroxylumisterol$_2$, 1,25-dihydroxylumisterol$_3$, 1-hydroxytachysterol$_2$, 1-hydroxytachysterol$_3$, 1-hydroxylumisterol$_2$, and 1-hydroxylumisterol$_3$. Also included are the 20- and 22-oxa tachysterol and lumisterol derivatives including 20-oxa-1α(OH)tachysterol$_2$, 20-oxa-1α(OH)tachysterol$_3$, 20-oxa-1α(OH)lumisterol$_2$, 20-oxa-1α(OH)lumisterol$_3$, 20-oxa-1α,2-5(OH)$_2$tachysterol$_2$, 20-oxa-1α,25(OH)$_2$tachysterol$_3$, 20-oxa-1α,25(OH)$_2$lumisterol$_2$, 20-oxa-1α,25(OH)$_2$lumisterol$_3$, 22-oxa-1α(OH)tachysterol$_2$, 22-oxa-1α(OH)tachysterol$_3$, 22-oxa-1α(OH)lumisterol$_2$, 22-oxa-1α(OH)lumisterol$_3$, 22-oxa-1α,25(OH)$_2$tachysterol$_2$, 22-oxa-1α,25(OH)$_2$tachysterol$_3$, 22-oxa-1α,2-5(OH)$_2$lumisterol$_2$ and 22-oxa-1α,25(OH)$_2$lumisterol$_3$. Also included within the scope of the present invention are 25,26 cyclopropyl compounds including 1,24-dihydroxy-25,26-dehydrotachysterol$_3$, 1,24-dihydroxy-25,26-dehydrotachysterol$_2$, 1,24-dihydroxy-25,26-dehydrolumisterol$_3$, and 1,24-dihydroxy-25,26-dehydrolumisterol$_2$.

Foremost among the individuals which may be treated with the compositions of the invention are humans, although the invention is not intended to be so limited. Any animal which may benefit from treatment with the compositions of the invention are within the spirit and scope of the present invention.

By using tachysterol and lumisterol analogs in topical compositions according to this invention, it is possible for the first time to provide a method which allows individuals living in regions of low sunlight to produce vitamin D analogs via their skin. The compositions of the present invention may be used, therefore, in methods of treating decubitus and diabetic foot ulcers; ulcerative keratitis; treating psoriasis; wound healing; inhibiting scar formation; treating or preventing osteodystrophy due to an acquired or inherited disorder in vitamin D metabolism; glucocorticoid-induced decrease in calcium absorption; osteoporosis; senile decrease in calcium absorption; hypoparathyroidism; milk fever disease; and turkey weak leg disease.

The compounds of the present invention can be administered in any appropriate pharmacological carrier for topical or intravenous administration. The dosage administered will be dependent on the age, health and weight of the recipient, and the nature of the effect desired.

The topical compositions of the invention may be applied so that at least 0.1 microgram, preferably at least about 10 micrograms to about 100 mg of the vitamin D precursor/gm carrier is administered to the skin. A preferred range is between about 1 microgram to about 1 milligram of tachysterol analog or lumisterol analog/gm carrier.

The compositions of the invention formulated for intravenous administration may comprise at least about 0.1 microgram, preferably at least about 1.0 microgram to about 100 mg of the vitamin D precursor per ml of physiologically acceptable solution. A most preferred range is about 1.0 micrograms to about 100 micrograms of tachysterol analog or lumisterol analog per ml of solution.

The compounds can be employed in a pharmacologically inert topical carrier such as one comprising a gel, an ointment or a cream, including such carriers as water, glycerol, alcohol, propylene glycol, fatty alcohols, triglycerides, fatty acid esters or mineral oils. Other possible carriers are liquid petrolatum, isopropylpalmitate, polyethylene glycol ethanol 95%, polyoxyethylene monolaurate 5% in water, sodium lauryl sulfate 5% in water, and the like. Minerals such as anti-oxidants, humectants, viscosity stabilizers and the like may be added, if necessary.

Alternatively, the compounds may be employed as part of a sun screen lotion which selectively screens the harmful high energy UV radiation (below 315 nm) but which allows medium and low energy UV radiation (above 315 nm) to pass which is of sufficient energy to photoisomerize lumisterol and tachysterol analogs to previtamin D analogs. Alternatively, the lumisterol and tachysterol analogs may be added to broad range sun screens that absorb radiation with energies of up to 360 nm. Such sun screen lotions may comprise any of those well known to those of ordinary skill in the art, for example, ethyl p-aminobenzoate (benzocaine), p-aminobenzoic acid (PABA), octyl methoxycinnamate (PARASOL® MCX), butyl methoxydibenzoylmethane (PARASOL® 1789), phenyl salicylate (salcol), 2-ethoxyethyl p-methoxycinnamate, glyceryl p-aminobenzoate, 2,4-dibenzoyl resorcinol, octyl dimethyl PABA, oxybenzone, benzophenones, methyl anthranilate, cinoxate, amyldimethyl PABA, homomenthyl salicylate, digalloyl trioleate, ethyl-p-glycosylimido benzoate, and red veterinary petrolatum. For other examples, see Algra et al., *Int. J. Derm.* 17:628–634 (1978), Sayre, R. M. et al., *Photochem. Photobiol.* 29:559–566 (1979).

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, anti-oxidants, chelating agents, inert gases and the like. See, generally, *Remington's Pharmaceutical Science*, 16th Ed., Mack Eds., 1980.

The compositions comprising tachysterol and/or lumisterol analogs which are formulated for parenteral administration may be utilized to provide an individual with these vitamin D analog precursors so as to allow the production of vitamin D analogs in the skin in the presence of medium and low energy UV radiation.

The invention further relates to solutions comprising the tachysterol and lumisterol analogs which may be exposed to UV radiation to allow the preparation of a solution comprising a vitamin D desired just before administration to the individual. This method avoids the decomposition of vitamin D analogs which occurs in solutions of vitamin D analogs. Solutions which may comprise tachysterol and lumisterol analogs may include the above-listed parenteral solutions. Of course, the solutions comprising the lumisterol and tachysterol analogs must be stored in an opaque container to avoid premature conversion of tachysterol and lumisterol analogs to the corresponding vitamin D analog.

Having now generally described the invention, the same will be understood by reference to an example which is provided herein for purposes of illustration only and is not intending to be limited unless otherwise specified.

EXAMPLE 1

Figure 2A:
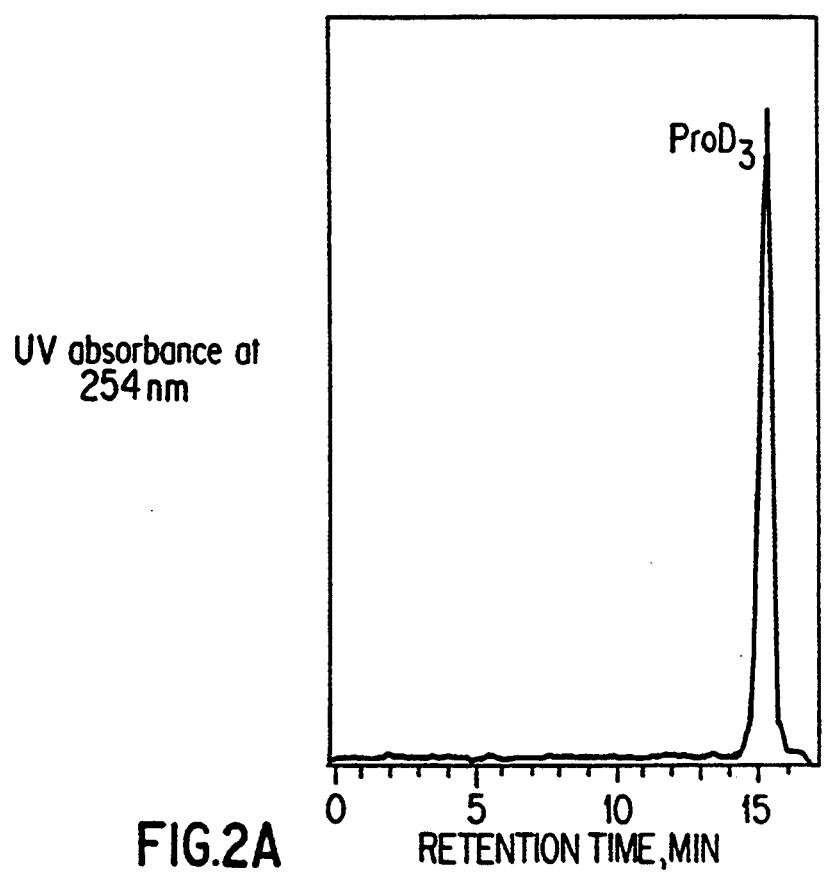
FIGS. 2(A and B) depict an HPLC trace of a control solution of provitamin $D_3$ (A) and a solution of provitamin $D_3$ exposed to sunlight on a day during the winter (B).
Figure 2B:
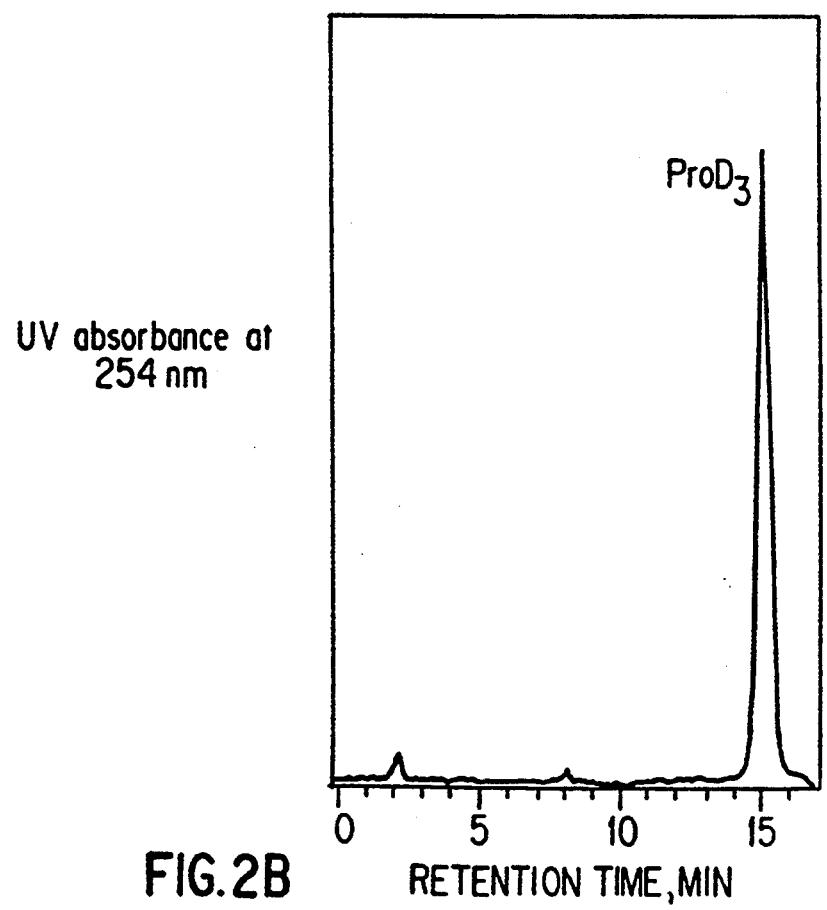
Figure 3A:
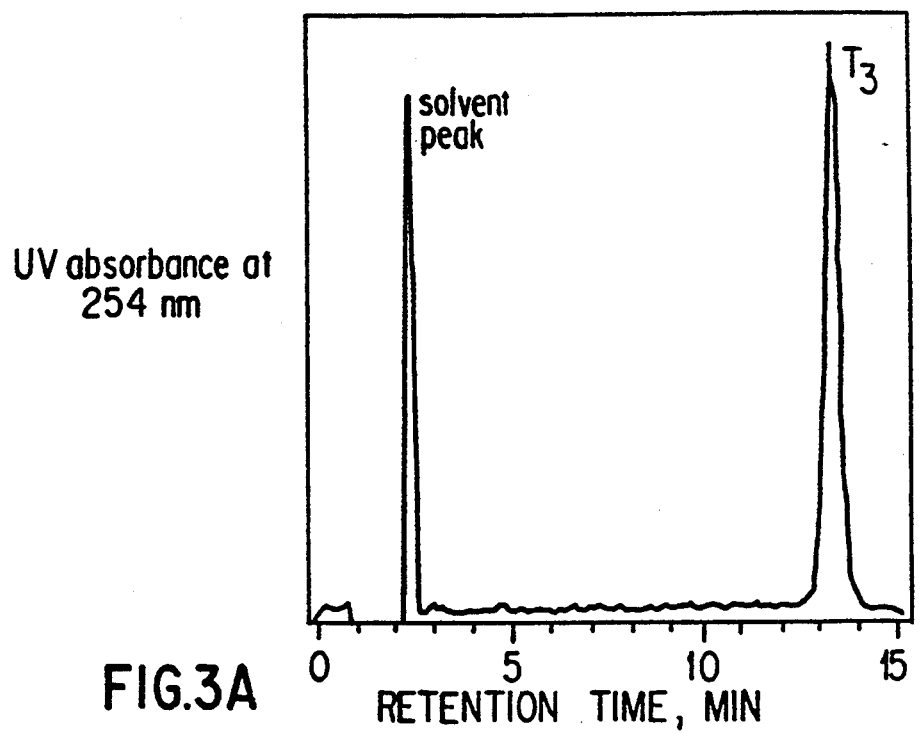
FIGS. 3(A and B) depict an HPLC trace of a control solution of tachysterol (A) and a solution of tachysterol exposed to sunlight on a day during the winter (B).
Figure 3B:
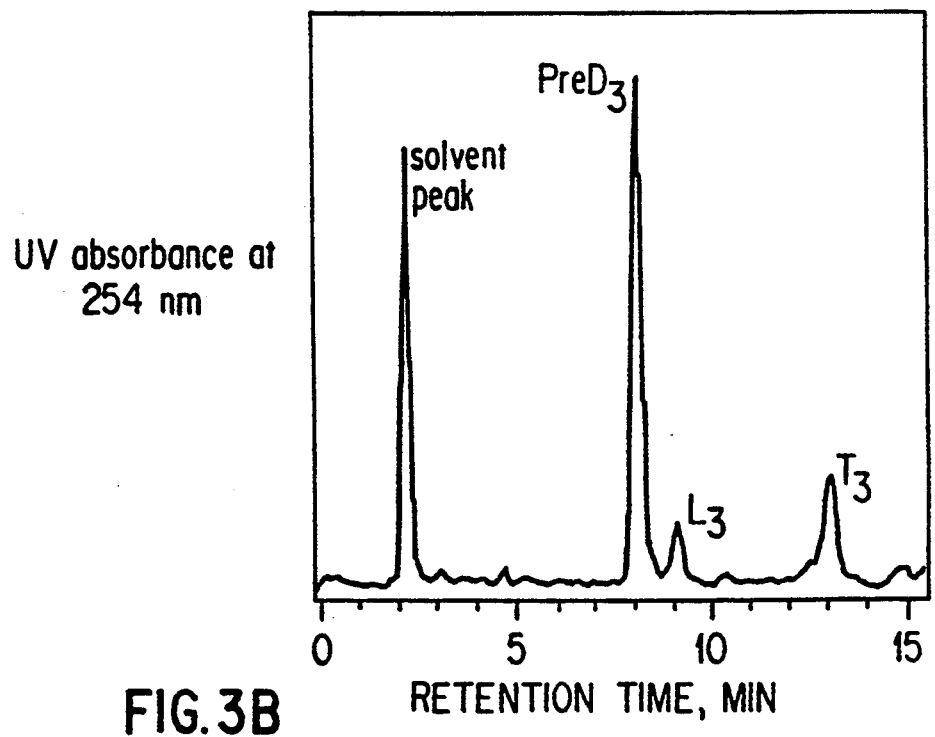
Figure 4A:
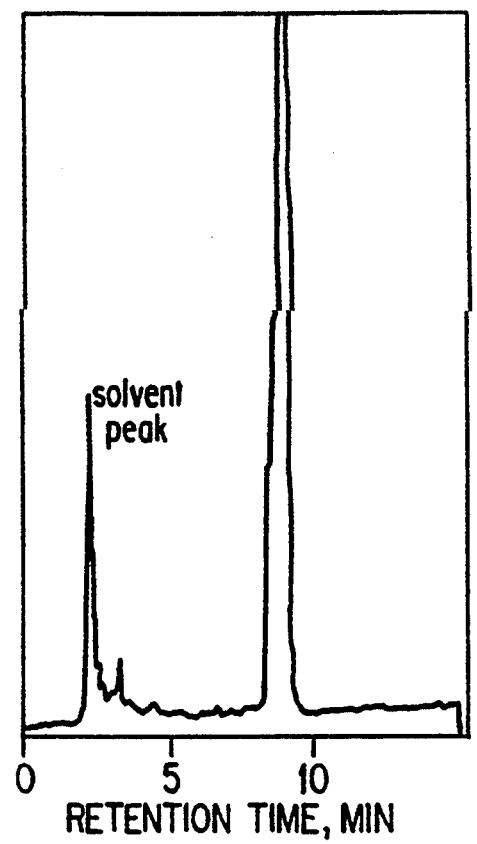
FIGS. 4(A and B) depict an HPLC trace of a control solution of lumisterol (A) and a solution of lumisterol exposed to sunlight on a day during the winter (B).
Figure 4B:
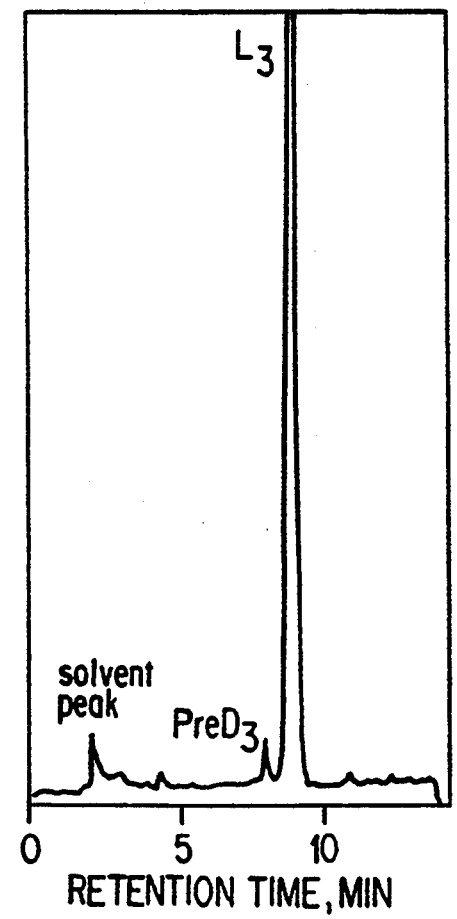

Crystalline provitamin D3 was dissolved in methanol at a concentration of 10 micrograms/ml. Ten ml of this solution was placed in quartz test tubes. One test tube containing provitamin D3 in methanol was exposed to direct sunlight in Boston during November, 1989 between 9 AM and 10 AM (FIG. 2B) while a similar sample remained in the dark over the same period of time (FIG. 2A). At the end of the exposure, a small aliquot was taken from each test tube and chromatographed on a high performance liquid chromatograph according to MacLaughlin et al., *Science* 216:1001–1003 (1982). Similar studies were conducted with lumisterol (FIG. 4) and tachysterol (FIG. 3) that were prepared as previously described (Holick et al., *Biochem.* 18:1003–1008 (1979). The analysis of all the chromatograms in FIGS. 2–4 revealed that when tachysterol and lumisterol were exposed to sunlight in November between 9 and 10 AM, they underwent photoisomerization to previtamin D3 (FIGS. 3B, 4B). In contrast, provitamin D3 exposed to the same direct sunlight did not convert to previtamin D3 (FIG. 2B). All samples that were kept in the dark for the same time did not convert to previtamin D3 (FIGS. 2A, 3A, 4A).

It is expected that the tachysterol and lumisterol analogs of the present invention, upon irradiation with the same low intensity and energy UV light, will give the corresponding previtamin D analogs.

Having now generally described this invention, it will be apparent to one of ordinary skill in the art that the same can be carried out in a variety of embodiments and variations which are equivalent without affecting the spirit or scope of the invention or any embodiments thereof.

What is claimed is:

1. A composition comprising a pharmaceutically acceptable carrier and an effective amount of a compound of the formula

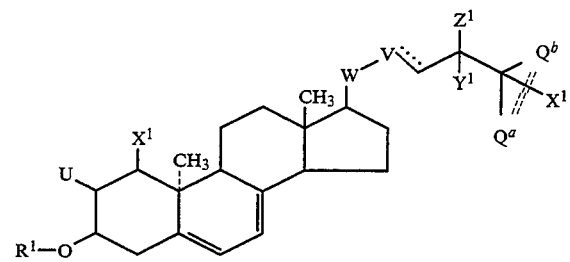

wherein the bond between carbons C-22 and C-23 is single or double bond;

Y$^1$ is hydrogen, F, CH$_3$, CH$_2$CH$_3$ or X$^1$;

U is hydrogen, —OH or —O—(C$_2$-C$_4$ alkyl)-OH;

Z$^1$ is F, H or X$^1$;

Q$^a$ is CF$_3$ or CH$_2$X$^1$;

Q$^b$ is CF$_3$ or CH$_3$;

wherein X$^1$ is selected from the group consisting of hydrogen, —OH and OR$^1$;

wherein R$^1$ is hydrogen or a straight or branched chain glycosidic residue containing 1-20 glycosidic units per residue, or R$^1$ is an orthoester glycoside moiety of the formula:

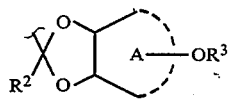

wherein A represents a glucofuranosyl or glucopyranosyl ring;

$R^2$ is hydrogen, lower alkyl, or aryl, with the proviso that aryl is phenyl or phenyl substituted by chloro, fluoro, bromo, iodo, lower $C_1$–$C_4$ alkyl, $C_1$–$C_4$ alkoxy; or naphthyl; and $R^3$ is hydrogen or a straight or branched chain glycosidic residue containing 1–20 glycosidic units per residue;

W is CH—$CH_3$ or O;

V is $CH_2$ or O;

with the proviso that both W and V are not both O;

"===" is either a single bond between $Q^a$ and $Q^b$ or a hydrogen atom on $Q^a$ and $Q^b$; and with the further proviso that said compound is not a lumisterol or lumisterol glycoside.

2. The composition of claim 1, wherein said compound is 1alpha,25-dihydroxylumisterol$_3$, 1alpha,25-dihydroxylumisterol$_2$, 1alpha-hydroxylumisterol$_3$, 1alpha-hydroxylumisterol$_2$, 24,25-dihydroxylumisterol$_3$, 24,25-dihydroxylumisterol$_2$, 1,24-dihydroxylumisterol$_3$, 1,24-dihydroxylumisterol$_2$, or 1,24-dihydroxy-25,26-dehydrolumisterol$_3$.

3. The composition of claim 1, wherein said carrier is effective for topical administration.

4. The composition of claim 3, further comprising one or more sun screen agents.

5. The composition of claim 1, wherein said carrier is effective for parenteral administration.

6. The composition of claim 1, wherein said compound is present in an amount of 0.00001 to 10% by weight.

7. The composition of claim 1, wherein said compound is present in an amount of 0.0001 to 0.01% by weight.

* * * * *